US006379913B1

(12) United States Patent
Bandman et al.

(10) Patent No.: US 6,379,913 B1
(45) Date of Patent: **\*Apr. 30, 2002**

(54) HUMAN SERINE CARBOXYPEPTIDASE

(75) Inventors: Olga Bandman; Phillip R. Hawkins; Jennifer L. Hillman, all of Mountain View; Preeti Lal; Surya K. Goli, both of Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,689

(22) Filed: Apr. 26, 1999

Related U.S. Application Data

(62) Division of application No. 08/828,488, filed on Mar. 31, 1997, now Pat. No. 5,925,521.

(51) Int. Cl.[7] ............ C12N 9/48; C12N 15/57; C12Q 1/37

(52) U.S. Cl. ............ 435/24; 435/320.1; 435/252.3; 435/212; 424/94.63; 536/23.2

(58) Field of Search ............ 435/212, 252.3, 435/320.1, 24; 536/23.2; 424/94.63

(56) References Cited

PUBLICATIONS

GenBank Accession No. AA129401, Nov. 1996.*
GenBank Accession No. R88882, Nov. 1996.*
Galjart, N.J., et al., "Expression of cDNA Encoding the Human "Protective Protein" Associated with Lysosomal β–Galactosidase and Neuraminidase: Homolgy to Yeast Proteases", *Cell*, 54: 755–764 (1988).
Latchinian–Sadek, L., et al., "Secretion, purification and characterization of a soluble form of the yeast KEX1–encoded protein from insect–cell cultures", *Eur J. Biochem*, 219: 647–652 (1994).
Elsliger, M., et al., "Homologous Modeling of the Lysosomal Protective Protein/Carboxypeptidase L: Structural and Functional Implications of Mutations Identified in Galactosialidosis Patients", *Proteins: Structure, Function, and Genetics*, 18: 81–93 (1994).
Jackman, H.L., et al., A Peptidase in Human Platelets That Deamidates Tachykinins Probable Identity with Lysosomal "Protective Protein", *The Journal of Biological Chemistry*, 265(19): 11265–11272 (1990).
Shimmoto, M., et al., "Protective Protein Gene Mutations in Galactosialidosis", *J Clin. Invest.*, 91: 2393–2398 (1993).
Cho, W.L., et al., "An extraovarian protein accumulated in mosquito oocytes is a carboxypeptidase activated in embryos", *Proc Natl Acad Sci USA*, 88(23): 10821–10824 (1991).

Cho, W.L., et al., (GI 1718107) GenBank Sequence Database (Accession P42660), National Center for Biotechnology Information: National Library of Medicine, Bethesda, Maryland 20849.
Cho, W.L., et al., (GI 159555) GenBank Sequence Database (Accession M79452), National Center for Biotechnology Information: National Library of Medicine, Bethesda, Maryland 20849.
Cho, W.L., et al., (Gi 473361) GenBank Sequence Database (Accession M79452), National Center for Biotechnology Information: National Library of Medicine, Bethesda, Maryland 20849.
Deitsch, K.W., et al., (GI 945383) GenBank Sequence Database (Accession L46594), National Center for Biotechnology Information: National Library of Medicine, Bethesda, Maryland 20849.
Deitsch, K.W., et al., (GI 945382) GenBank Sequence Database (Accession L46594), National Center for Biotechnology Information: National Library of Medicine, Bethesda, Maryland 20849.
Galjart, N.J., et al., (GI 190283) GenBank Sequence Database (Accession M22960), National Center for Biotechnology Information: National Library of Medicine, Bethesda, Maryland 20849.
Galjart, N.J., et al., (GI 190282) GenBank Sequence Database (Accession M22960), National Center for Biotechnology Information: National Library of Medicine, Bethesda, Maryland 20849.
Hillier et al., (GI 1690795), GenBank Sequence Database (Accession AA133826), National Center for Biotechnology Information: National Library of Medicine, Bethesda, Maryland 20849.
Alcalde et al., *J. Autoimmunity* 9: 525–528 (1996).
EMBL/GenBank Databases Acc. No. AA234471 Sequence ref. HS1152814, Mar. 6, 1997, Hillier et al., "WasU–Merck EST Project 1997", XP002068353.
EMBL/GenBank Databases Acc. No. H10119 Sequence ref. HS119159, Jul. 2, 1995, Hillier et al., "The WasU–Merck EST Project", XP002068354.
EMBL/GenBank Databases Acc. No. AA114985 Sequence ref. HSAA14985, Nov. 16, 1996, Hillier et al., "The WasU–Merck EST Project", XP002068355.
EMBL/GenBank Databases Acc. No. AA151310 Sequence ref. HSAA51310, Dec. 15, 1996, Hillier et al., "The WasU–Merck EST Project", XP002068356.

* cited by examiner

Primary Examiner—Rebecca E. Prouty
(74) Attorney, Agent, or Firm—Incyte Genomics, Inc.

(57) ABSTRACT

The present invention provides a human serine carboxypeptidase (CPEPT) and polynucleotides which identify and encode CPEPT. The invention also provides expression vectors, host cells, agonists, antibodies, and antagonists. The invention also provides methods for treating disorders associated with expression of CPEPT.

20 Claims, 9 Drawing Sheets

```
5'                                                                                            54
   A AGC GCT GCA AGG ACA ACC GGC TGG GGT CCT TGC GCG CCG GGC TCA GGG AGG
                                                                                              108
AGC ACC GAC TGC GCC GCA CCC TGA GAG ATG GTT GGT GCC ATG TGG AAG GTG ATT
                                               M   V   G   A   M   W   K   V   I
                                                                                              162
GTT TCG CTG GTC CTG ATG TTG ATG CCT GGC CCC TGT GAT GGG CTG TTT CAC TCC CTA
 V   S   L   V   L   M   L   M   P   G   P   C   D   G   L   F   H   S   L
                                                                                              216
TAC AGA AGT GTT TCC ATG CCA CCT AAG GGA GAC TCA GGA CAG CCA TTA TTT CTC
 Y   R   S   V   S   M   P   P   K   G   D   S   G   Q   P   L   F   L
                                                                                              270
ACC CCT TAC ATT GAA GCT GGG AAG ATC CAA AAA AGA GAA TTG AGT TTG GTC
 T   P   Y   I   E   A   G   K   I   Q   K   R   E   L   S   L   V
                                                                                              324
GGT CCT TTC CCA GGA CTG AAC ATG AAG AGT TAT GCC GAC TTC CTC ACT GTG AAT
 G   P   F   P   G   L   N   M   K   S   Y   A   D   F   L   T   V   N
                                                                                              378
AAG ACT TAC AAC AGC AAC CTC TTC TTC TGG TTC TTC CCA GCT CAG ATA CAG CCA
 K   T   Y   N   S   N   L   F   F   W   F   F   P   A   Q   I   Q   P
```

FIGURE 1A

```
        387      396      405      414      423      432
GAA GAT GCC CCA GTA GTT CTC TGG CTA CAG GGT GAG CCG GGA GGT TCA TCC ATG
 E   D   A   P   V   V   L   W   L   Q   G   E   P   G   G   S   S   M 441      450      459      468      477      486
TTT GGA CTC TTT GTG GAA CAT GGG CCT TAT GTT GTC ACA AGT AAC ATG ACC TTG
 F   G   L   F   V   E   H   G   P   Y   V   V   T   S   N   M   T   L 495      504      513      522      531      540
CGT GAC AGA GAC TTC CCC TGG ACC ACA ACG CTC TCC ATG CTT TAC ATT GAC AAT
 R   D   R   D   F   P   W   T   T   T   L   S   M   L   Y   I   D   N 549      558      567      576      585      594
CCA GTG GGC ACA GGC TTC AGT TTT ACT GAT GAT ACC CAC GGA TAT GCA GTC AAT
 P   V   G   T   G   F   S   F   T   D   D   T   H   G   Y   A   V   N 603      612      621      630      639      648
GAG GAC GAT GTA GCA CGG GAT TTA TAC AGT GCA CTA ATT CAG TTT TTC CAG ATA
 E   D   D   V   A   R   D   L   Y   S   A   L   I   Q   F   F   Q   I 657      666      675      684      693      702
TTT CCT GAA TAT AAA AAT AAT GAC TTT TAT GTC ACT GGG GAG TCT TAT GCA GGG
 F   P   E   Y   K   N   N   D   F   Y   V   T   G   E   S   Y   A   G 711      720      729      738      747      756
AAA TAT GTG CCA GCC ATT GCA CAC CTC ATC CAT TCC CTC AAC CCT GTG AGA GAG
 K   Y   V   P   A   I   A   H   L   I   H   S   L   N   P   V   R   E
```

FIGURE 1B

```
      765                774                783                792                801                810
GTG AAG ATC AAC CTG AAC GGA ATT GCT ATT GGA GAT GGA TAT TCT GAT CCC GAA
 V   K   I   N   L   N   G   I   A   I   G   D   G   Y   S   D   P   E 819                828                837                846                855                864
TCA ATT ATA GGG GGC TAT GCA GAA TTC CTG TAC CAA ATT GGC TTG TTG GAT GAG
 S   I   I   G   G   Y   A   E   F   L   Y   Q   I   G   L   L   D   E 873                882                891                900                909                918
AAG CAA AAA AAG TAC TTC CAG AAG CAG TGC CAT GAA TGC ATA GAA CAC ATC AGG
 K   Q   K   K   Y   F   Q   K   Q   C   H   E   C   I   E   H   I   R 927                936                945                954                963                972
AAG CAG AAC TGG TTT GAG GCC TTT GAA ATA CTG GAT AAA CTA CTA GAT GGC GAC
 K   Q   N   W   F   E   A   F   E   I   L   D   K   L   L   D   G   D 981                990                999               1008               1017               1026
TTA ACA AGT GAT CCT TCT TAC TTC CAG AAT GTT ACA GGA TGT AGT AAT TAC TAT
 L   T   S   D   P   S   Y   F   Q   N   V   T   G   C   S   N   Y   Y 1035               1044               1053               1062               1071               1080
AAC TTT TTG CGG TGC ACG GAA CCT GAG GAT CAG CTT TAC TAT GTG AAA TTT TTG
 N   F   L   R   C   T   E   P   E   D   Q   L   Y   Y   V   K   F   L 1089               1098               1107               1116               1125               1134
TCA CTC CCA GAG AGA CAA GCC ATC CAC GTG GGG AAT CAG ACT TTT AAT GAT
 S   L   P   E   R   Q   A   I   H   V   G   N   Q   T   F   N   D
```

FIGURE 1C

```
                  1143           1152           1161           1170           1179                  1188
                  GGA ACT ATA GTT GAA AAG TAC TTG CGA GAA GAT ACA GTA CAG TCA GTT AAG CCA
                   G   T   I   V   E   K   Y   L   R   E   D   T   V   Q   S   V   K   P 1197           1206           1215           1224           1233                  1242
            TGG TTA ACT GAA ATC ATG AAT AAT AAG TAT CTG ATC TAC AAT GGC CAA CTG
             W   L   T   E   I   M   N   N   K   Y   L   I   Y   N   G   Q   L 1251           1260           1269           1278           1287                  1296
      GAC ATC ATC GTG GCA GCT GCC CTG ACA GAG CGC TCC TTG ATG GGC ATG GAC TGG
       D   I   I   V   A   A   A   L   T   E   R   S   L   M   G   M   D   W 1305           1314           1323           1332           1341                  1350
            AAA GGA TCC CAG GAA TAC AAG GCA GAA AAA AAA AAA GTT TGG AAG ATC TTT
             K   G   S   Q   E   Y   K   A   E   K   K   K   V   W   K   I   F 1359           1368           1377           1386           1395                  1404
      AAA TCT GAC AGT GGA GTG GCT GGA GTG TAC ATC CGG CAA GTG GGT GAC TTC CAT CAG
       K   S   D   S   G   V   A   G   V   Y   I   R   Q   V   G   D   F   H   Q 1413           1422           1431           1440           1449                  1458
            GTA ATT ATT CGA GGT GGA GGA CAT ACT TTA CCC TAT GAC CAG CCT CTG AGA GCT
             V   I   I   R   G   G   G   H   T   L   P   Y   D   Q   P   L   R   A 1467           1476           1485           1494           1503                  1512
      TTT GAC ATG ATT AAT CGA TTC ATT TAT GGA AAA GGA TGG GAT CCT TAT GTT GGA
       F   D   M   I   N   R   F   I   Y   G   K   G   W   D   P   Y   V   G
```

FIGURE 1D

```
     1521      1530      1539      1548      1557      1566
TAA ACT ACC TTC CCA AAA GAG AAC ATC AGA GGT TTT CAT TGC TGA AAA GAA AAT 1575      1584      1593      1602      1611      1620
CGT AAA AAC AGA AAA TGT CAT AGG AAT AAA AAA ATT ATC TTT TCA TAT CTG CAA 1629      1638      1647      1656      1665
GAT CTT TTT CAT CAA TAA AAA TTA TCC TTG AAA CAA AAA AAA AAA GAA AAA G 3'
```

FIGURE 1E

| | | | | | | | | |
|---|---|---|---|---|---|---|---|---|
| 1 | M V – – – – – – – – | – – – – – – – G A M W K V I V S L V L L M P G P C D G L | – – – – – – – – – – – – – – – – – – – – – – | – – – F H S L Y R S V | SEQ ID NO:1 |
| 1 | M V – – – – – – – – | – – – – – – – G A M W K V I V S L V L L M P G P C D G L | – – – – – – – – – – – – – – – – – – – – – – | – – – F H S L Y R S V | SEQ ID NO:3 |
| 1 | M V – – – – – – – – | – – – – – – – G A M W K V I V S L V L L M P G P C G G L | – – – – – – – – – – – – – – – – – – – – – – | – – – F H S L Y R S V | SEQ ID NO:5 |
| 1 | M V – – – – – – – – | – – K F H L L V – L I A F T C Y T C S D A T L W N P Y K K L M R G S | | | GI 1718107 |
| 1 | M I R A A P P P L F L L L L L L L V S | – – – – – – – – – – – – – – – – – – – – – – W A S | – – – – – – – – – – – – – – – – – – – – – – | – – – – – – R G E | GI 190283 |
| 32 | S M P P K – – – | – – – – – – – G D S G Q P L F L T P Y I E A G K I Q K G R E L | S L V G P F P G L N | | SEQ ID NO:1 |
| 32 | S M P P K – – – | – – – – – – – G D S G Q P L F L T P Y I E A G K I Q K G R E L | S L V G P F P G L N | | SEQ ID NO:3 |
| 32 | S M P P K – – – | – – – – – – – G D S G Q P L F L T P Y I E A G K I | – – – – – – – – – – – – – – – – – – – – – – | | SEQ ID NO:5 |
| 34 | A S P P R P G E | S G E P L F L T P L L Q D G K I E E A R N K A R V N H – P M L S | | | GI 1718107 |
| 28 | A A P – – – – – | – – – – – – – – – – – – – – D Q D E I Q R L P G L A K Q P S F – – – | | | GI 190283 |
| 71 | – M K S Y A D F L T V N K T Y N S N L F F W F | F P A Q I Q P E D A P V V L W L Q | | | SEQ ID NO:1 |
| 71 | – M K S Y A G F L T V N K T Y N S N L F F W F | F P A Q I Q P E D A P V V L W L Q | | | SEQ ID NO:3 |
| 55 | – – – – – – – – – – – – – – – – – – – – – – – – – – – – – – – | – – – – – – – – – – – – – – – – – – – – – – | | | SEQ ID NO:5 |
| 73 | S V E S Y S G F M T V D A K H N S N L F F W Y V P A K N N R E Q A P I L V W L Q | | | | GI 1718107 |
| 48 | – – R Q Y S G Y L – – K S S G S K H L H Y W F V E S Q K D P E N S P V V L W L N | | | | GI 190283 |
| 110 | G E P G G S S M F G L F V E H G P Y V V T S N | – M T L R D R D F P W T T T L S M | | | SEQ ID NO:1 |
| 110 | G G P G G S S M X G L F V E H G P Y V V T S N | – M T L R D R D F P W T T T X S M | | | SEQ ID NO:3 |
| 55 | – – – – – – – – – – – – – – – – – – – – – – – – – – – – – – – | – – – – – – – – – – – – – – – – – – – – – – | | | SEQ ID NO:5 |
| 113 | G G P G A S S L F G M E E N G P F H I H R N – K S V K Q R E Y S W H Q N H H M | | | | GI 1718107 |
| 84 | G G P G C S S L D G L L T E H G P F L V Q P D G V T L E Y N P Y S W N L I A N V | | | | GI 190283 |

```
304  Y F Q N V T G C S N Y Y N F L R C T E - - - - - - - - - P E D Q L Y Y V K F L S L P E V R Q A -   SEQ ID NO:1
304  Y F Q N V T G C S N Y Y N F L R C T E - - - - - - - - - P E D Q L Y Y V K F L S L P E V R Q A -   SEQ ID NO:3
179  Y F Q N V T G C S N Y Y N F L R C T E - - - - - - - - - P E D Q L Y Y V K F L S L P E V R Q A -   SEQ ID NO:5
303  Y F K K V T G F S Y Y N F I K G D E E S K Q D S V L M E F L S N P E V R K G - GI 1718107
278  Y A P C A G G V P S H F R Y E K D T V V V Q D L G N I F T R L P L K R M W H Q A   GI 190283

342  - I H V G N Q T F N D G - - T - - - - - - - - - - - - - I V E K Y L R E -     SEQ ID NO:1
342  - I H V G N Q T F N D G - - T - - - - - - - - - - - - - I V E K Y L R E -     SEQ ID NO:3
217  - I H V G N Q T F N D G - - T - - - - - - - - - - - - - I V E K Y L R E -     SEQ ID NO:5
342  - I H V G E L P F H D S - - - - - - - - - - - - - - - - I V E K V A E M L S E - GI 1718107
318  L L R S G D K V R M D P P C T N T T A A S T Y L N N P Y V R K A L N I P E Q L P   GI 190283

369  P W - L T E I M - - - - - - - - - - - - - - - - - - - - - - - D T V Q S V K     SEQ ID NO:1
369  P W - L T E I M - - - - - - - - - - - - - - - - - - - - - - - D T V Q S V K     SEQ ID NO:3
244  P W - L T E I M - - - - - - - - - - - - - - - - - - - - - - - D T V Q S V K     SEQ ID NO:5
372  P W - V S K L L - - - - - - - - - - - - - - - - - - - - - - - D T L D T V A   GI 1718107
358  Q W D M C N F L V N L Q Y R R L Y R S M N S Q Y L K L L S S Q K Y Q I L L Y N G   GI 190283

386  Q L D I I V A A A L T E R S L M G M D W K G S Q E Y K K A E - - - K K K V W K I - - F   SEQ ID NO:1
386  Q L D I I V A A A L T E R S L M G M D W K G S Q E Y K K A E - - - K K K - V W K I - - F   SEQ ID NO:3
261  Q L D I I V A A A L T E R S L M G M D W K G S Q E Y K K A E - - - K K K - V W K I - - F   SEQ ID NO:5
389  Q L D I I C A Y P M T V D F L M K M P F D G D S E Y K R A N - R E - - - H - - Y   GI 1718107
398  D V D M A C N - - - - - - - F M G D E W F V D S L N Q K M E V Q R R P W L V K Y   GI 190283
```

FIGURE 2C

```
424 -KSDSGVAGYIRQVGDFHQVIIRGGGHTLPYDQPLRAFDM   SEQ ID NO:1
423 -KSDSEVAGYIRQVGDFHQVIIRGGGHILPYDQPLRAFDM   SEQ ID NO:3
298 -KSDSEVAGYIRQVGDFHQVIIRGGGHILPYDQPLRAFDM   SEQ ID NO:5
423 -RVDGEIAGYKKRAGRLQEVLIRNAGHMVPRDQPKWAFDM   GI 1718107
431 GDSGEQIAGFVKEFSHIAFLTIKGAGHMVPTDKPLAAFTM   GI 190283

463 INRFIYGKGWDPYVG   SEQ ID NO:1
462 INRFIYGKGWDPYVG   SEQ ID NO:3
337 INRFIYGKGWDPYVG   SEQ ID NO:5
462 ITSFTHKN---YL    GI 1718107
471 FSRFLNK---QPY    GI 190283
```

FIGURE 2D

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 477 amino acids
       (B) TYPE: amino acid
       (C) STRANDEDNESS: single
       (D) TOPOLOGY: linear (vii) IMMEDIATE SOURCE:
       (A) LIBRARY: MPHGNOT03
       (B) CLONE: 443004

(xi) SEQUENCE DESCRIPTION: SEQ ID NO:1:

```
Met Val Gly Ala Met Trp Lys Val Ile Val Ser Leu Val Leu Leu Met
 1               5                  10                  15

Pro Gly Pro Cys Asp Gly Leu Phe His Ser Leu Tyr Arg Ser Val Ser
                20                  25                  30

Met Pro Pro Lys Gly Asp Ser Gly Gln Pro Leu Phe Leu Thr Pro Tyr
            35                  40                  45

Ile Glu Ala Gly Lys Ile Gln Lys Gly Arg Glu Leu Ser Leu Val Gly
50                  55                  60

Pro Phe Pro Gly Leu Asn Met Lys Ser Tyr Ala Asp Phe Leu Thr Val
65                  70                  75                  80

Asn Lys Thr Tyr Asn Ser Asn Leu Phe Phe Trp Phe Phe Pro Ala Gln
                85                  90                  95

Ile Gln Pro Glu Asp Ala Pro Val Val Leu Trp Leu Gln Gly Glu Pro
            100                 105                 110

Gly Gly Ser Ser Met Phe Gly Leu Phe Val Glu His Gly Pro Tyr Val
            115                 120                 125

Val Thr Ser Asn Met Thr Leu Arg Asp Arg Asp Phe Pro Trp Thr Thr
130                 135                 140

Thr Leu Ser Met Leu Tyr Ile Asp Asn Pro Val Gly Thr Gly Phe Ser
145                 150                 155                 160

Phe Thr Asp Asp Thr His Gly Tyr Ala Val Asn Glu Asp Asp Val Ala
                165                 170                 175

Arg Asp Leu Tyr Ser Ala Leu Ile Gln Phe Phe Gln Ile Phe Pro Glu
            180                 185                 190

Tyr Lys Asn Asn Asp Phe Tyr Val Thr Gly Glu Ser Tyr Ala Gly Lys
            195                 200                 205

Tyr Val Pro Ala Ile Ala His Leu Ile His Ser Leu Asn Pro Val Arg
210                 215                 220

Glu Val Lys Ile Asn Leu Asn Gly Ile Ala Ile Gly Asp Gly Tyr Ser
225                 230                 235                 240

Asp Pro Glu Ser Ile Ile Gly Gly Tyr Ala Glu Phe Leu Tyr Gln Ile
                245                 250                 255

Gly Leu Leu Asp Glu Lys Gln Lys Tyr Phe Gln Lys Gln Cys His
            260                 265                 270

Glu Cys Ile Glu His Ile Arg Lys Gln Asn Trp Phe Glu Ala Phe Glu
            275                 280                 285

Ile Leu Asp Lys Leu Leu Asp Gly Asp Leu Thr Ser Asp Pro Ser Tyr
290                 295                 300
```

```
Phe Gln Asn Val Thr Gly Cys Ser Asn Tyr Tyr Asn Phe Leu Arg Cys
305                 310                 315                 320

Thr Glu Pro Glu Asp Gln Leu Tyr Tyr Val Lys Phe Leu Ser Leu Pro
            325                 330                 335

Glu Val Arg Gln Ala Ile His Val Gly Asn Gln Thr Phe Asn Asp Gly
            340                 345                 350

Thr Ile Val Glu Lys Tyr Leu Arg Glu Asp Thr Val Gln Ser Val Lys
            355                 360                 365

Pro Trp Leu Thr Glu Ile Met Asn Asn Tyr Lys Val Leu Ile Tyr Asn
    370                 375                 380

Gly Gln Leu Asp Ile Ile Val Ala Ala Ala Leu Thr Glu Arg Ser Leu
385                 390                 395                 400

Met Gly Met Asp Trp Lys Gly Ser Gln Glu Tyr Lys Lys Ala Glu Lys
                405                 410                 415

Lys Lys Val Trp Lys Ile Phe Lys Ser Asp Ser Gly Val Ala Gly Tyr
            420                 425                 430

Ile Arg Gln Val Gly Asp Phe His Gln Val Ile Ile Arg Gly Gly Gly
            435                 440                 445

His Thr Leu Pro Tyr Asp Gln Pro Leu Arg Ala Phe Asp Met Ile Asn
    450                 455                 460

Arg Phe Ile Tyr Gly Lys Gly Trp Asp Pro Tyr Val Gly
465                 470                 475

(2) INFORMATION FOR SEQ ID NO:2:

(i) SEQUENCE CHARACTERISTICS:
        (A) LENGTH: 1670 base pairs
        (B) TYPE: nucleic acid
        (C) STRANDEDNESS: single
        (D) TOPOLOGY: linear (vii) IMMEDIATE SOURCE:
        (A) LIBRARY: MPHGNOT03
        (B) CLONE: 443004

(xi) SEQUENCE DESCRIPTION: SEQ ID NO:2:

AAGCGCTGCA AGGACAACCG GCTGGGGTCC TTGCGCGCCG GGCTCAGGGA GGAGCACCGA      60

CTGCGCCGCA CCCTGAGAGA TGGTTGGTGC CATGTGGAAG GTGATTGTTT CGCTGGTCCT     120

GTTGATGCCT GGCCCCTGTG ATGGGCTGTT TCACTCCCTA TACAGAAGTG TTTCCATGCC     180

ACCTAAGGGA GACTCAGGAC AGCCATTATT TCTCACCCCT TACATTGAAG CTGGGAAGAT     240

CCAAAAAGGA AGAGAATTGA GTTTGGTCGG TCCTTTCCCA GGACTGAACA TGAAGAGTTA     300

TGCCGACTTC CTCACTGTGA ATAAGACTTA CAACAGCAAC CTCTTCTTCT GGTTCTTCCC     360

AGCTCAGATA CAGCCAGAAG ATGCCCCAGT AGTTCTCTGG CTACAGGGTG AGCCGGGAGG     420

TTCATCCATG TTTGGACTCT TGTGGAACA TGGGCCTTAT GTTGTCACAA GTAACATGAC      480

CTTGCGTGAC AGAGACTTCC CCTGGACCAC AACGCTCTCC ATGCTTTACA TTGACAATCC     540

AGTGGGCACA GGCTTCAGTT TTACTGATGA TACCCACGGA TATGCAGTCA ATGAGGACGA     600

TGTAGCACGG GATTTATACA GTGCACTAAT TCAGTTTTTC CAGATATTTC TGAATATAA      660

AAATAATGAC TTTTATGTCA CTGGGGAGTC TTATGCAGGG AAATATGTGC AGCCATTGC      720

ACACCTCATC CATTCCCTCA ACCCTGTGAG AGAGGTGAAG ATCAACCTGA ACGGAATTGC     780

TATTGGAGAT GGATATTCTG ATCCCGAATC AATTATAGGG GGCTATGCAG AATTCCTGTA     840

CCAAATTGGC TTGTTGGATG AGAAGCAAAA AAAGTACTTC CAGAAGCAGT GCCATGAATG     900

CATAGAACAC ATCAGGAAGC AGAACTGGTT TGAGGCCTTT GAAATACTGG ATAAACTACT     960
```

-continued

```
AGATGGCGAC TTAACAAGTG ATCCTTCTTA CTTCCAGAAT GTTACAGGAT GTAGTAATTA   1020

CTATAACTTT TTGCGGTGCA CGGAACCTGA GGATCAGCTT TACTATGTGA AATTTTTGTC   1080

ACTCCCAGAG GTGAGACAAG CCATCCACGT GGGGAATCAG ACTTTTAATG ATGGAACTAT   1140

AGTTGAAAAG TACTTGCGAG AAGATACAGT ACAGTCAGTT AAGCCATGGT TAACTGAAAT   1200

CATGAATAAT TATAAGGTTC TGATCTACAA TGGCCAACTG GACATCATCG TGGCAGCTGC   1260

CCTGACAGAG CGCTCCTTGA TGGGCATGGA CTGGAAAGGA TCCCAGGAAT ACAAGAAGGC   1320

AGAAAAAAAA AAAGTTTGGA AGATCTTTAA ATCTGACAGT GGAGTGGCTG GTTACATCCG   1380

GCAAGTGGGT GACTTCCATC AGGTAATTAT TCGAGGTGGA GGACATACTT TACCCTATGA   1440

CCAGCCTCTG AGAGCTTTTG ACATGATTAA TCGATTCATT TATGGAAAAG GATGGGATCC   1500

TTATGTTGGA TAAACTACCT TCCCAAAAGA GAACATCAGA GGTTTTCATT GCTGAAAAGA   1560

AAATCGTAAA AACAGAAAAT GTCATAGGAA TAAAAAAATT ATCTTTTCAT ATCTGCAAGA   1620

TCTTTTTCAT CAATAAAAAT TATCCTTGAA ACAAAAAAAA AAAGAAAAAG              1670
```

(2) INFORMATION FOR SEQ ID NO:3:

(i) SEQUENCE CHARACTERISTICS:
        (A) LENGTH: 476 amino acids
        (B) TYPE: amino acid
        (C) STRANDEDNESS: single
        (D) TOPOLOGY: linear (vii) IMMEDIATE SOURCE:
        (A) LIBRARY: MMLR3DT01
        (B) CLONE: 566993

(xi) SEQUENCE DESCRIPTION: SEQ ID NO:3:

```
Met Val Gly Ala Met Trp Lys Val Ile Val Ser Leu Val Leu Leu Met
 1               5                  10                  15

Pro Gly Pro Cys Asp Gly Leu Phe His Ser Leu Tyr Arg Ser Val Ser
                20                  25                  30

Met Pro Pro Lys Gly Asp Ser Gly Gln Pro Leu Phe Leu Thr Pro Tyr
            35                  40                  45

Ile Glu Ala Gly Lys Ile Gln Lys Gly Arg Glu Leu Ser Leu Val Gly
        50                  55                  60

Pro Phe Pro Gly Leu Asn Met Lys Ser Tyr Ala Gly Phe Leu Thr Val
65                  70                  75                  80

Asn Lys Thr Tyr Asn Ser Asn Leu Phe Phe Trp Phe Phe Pro Ala Gln
                85                  90                  95

Ile Gln Pro Glu Asp Ala Pro Val Val Leu Trp Leu Gln Gly Gly Pro
            100                 105                 110

Gly Gly Ser Ser Met Xaa Gly Leu Phe Val Glu His Gly Pro Tyr Val
        115                 120                 125

Val Thr Ser Asn Met Thr Leu Arg Asp Arg Asp Phe Pro Trp Thr Thr
    130                 135                 140

Thr Xaa Ser Met Leu Tyr Ile Asp Asn Pro Val Gly Thr Gly Phe Ser
145                 150                 155                 160

Phe Thr Asp Asp Thr His Gly Tyr Ala Val Asn Glu Asp Asp Val Ala
                165                 170                 175

Arg Asp Leu Tyr Ser Ala Leu Ile Gln Phe Phe Gln Ile Phe Pro Glu
            180                 185                 190

Tyr Lys Asn Asn Asp Phe Tyr Val Thr Gly Glu Ser Tyr Ala Gly Lys
        195                 200                 205
```

-continued

```
Tyr Val Pro Ala Ile Ala His Leu Ile His Ser Leu Asn Pro Val Arg
    210                 215                 220

Glu Val Lys Ile Asn Leu Asn Gly Ile Ala Ile Gly Asp Gly Tyr Ser
225                 230                 235                 240

Asp Pro Glu Ser Ile Ile Gly Gly Tyr Ala Glu Phe Leu Tyr Gln Ile
                245                 250                 255

Gly Leu Leu Asp Glu Lys Gln Lys Lys Tyr Phe Gln Lys Gln Cys His
                260                 265                 270

Glu Cys Ile Glu His Ile Arg Lys Gln Asn Trp Phe Glu Ala Phe Glu
            275                 280                 285

Ile Leu Asp Lys Leu Leu Asp Gly Asp Leu Thr Ser Asp Pro Ser Tyr
    290                 295                 300

Phe Gln Asn Val Thr Gly Cys Ser Asn Tyr Tyr Asn Phe Leu Arg Cys
305                 310                 315                 320

Thr Glu Pro Glu Asp Gln Leu Tyr Tyr Val Lys Phe Leu Ser Leu Pro
                325                 330                 335

Glu Val Arg Gln Ala Ile His Val Gly Asn Gln Thr Phe Asn Asp Gly
                340                 345                 350

Thr Ile Val Glu Lys Tyr Leu Arg Glu Asp Thr Val Gln Ser Val Lys
            355                 360                 365

Pro Trp Leu Thr Glu Ile Met Asn Asn Tyr Lys Val Leu Ile Tyr Asn
    370                 375                 380

Gly Gln Leu Asp Ile Ile Val Ala Ala Ala Leu Thr Glu Arg Ser Leu
385                 390                 395                 400

Met Gly Met Asp Trp Lys Gly Ser Gln Glu Tyr Lys Lys Ala Glu Lys
                405                 410                 415

Lys Val Trp Lys Ile Phe Lys Ser Asp Ser Glu Val Ala Gly Tyr Ile
                420                 425                 430

Arg Gln Val Gly Asp Phe His Gln Val Ile Ile Arg Gly Gly His
            435                 440                 445

Ile Leu Pro Tyr Asp Gln Pro Leu Arg Ala Phe Asp Met Ile Asn Arg
    450                 455                 460

Phe Ile Tyr Gly Lys Gly Trp Asp Pro Tyr Val Gly
465                 470                 475
```

(2) INFORMATION FOR SEQ ID NO:4:

(i) SEQUENCE CHARACTERISTICS:
        (A) LENGTH: 1551 base pairs
        (B) TYPE: nucleic acid
        (C) STRANDEDNESS: single
        (D) TOPOLOGY: linear (vii) IMMEDIATE SOURCE:
        (A) LIBRARY: MMLR3DT01
        (B) CLONE: 566993

(xi) SEQUENCE DESCRIPTION: SEQ ID NO:4:

```
GAAAGCTGGT ACGCCTGCNG GTNCCGGTCC GGAATTCNCG GGTNGACCCA CGCGTCCGAN      60

CGACTGCGCC GCACCCTGAG AGATGGTTGG TGCCATGTGG AAGGTGATTG TTTCGCTGGT     120

CCTGTTGATG CCTGGCCCCT GTGATGGGCT GTTTCACTCC CTATACAGAA GTGTTTCCAT     180

GCCACCTAAG GGAGACTCAG GACAGCCATT ATTTCTCACC CCTTACATTG AAGCTGGGAA     240

GATCCAAAAA GGAAGAGAAT TGAGTTTGGT CGGCCCTTTC CCAGGACTGA ACATGAAGAG     300

TTATGCCGGC TTCCTCACCG TGAATAAGAC TTACAACAGC AACCTCTTCT TCTGGTTCTT     360

CCCAGCTCAG ATACAGCCAG AAGATGCCCC AGTAGTTCTC TGGCTACAGG GTGGGCCGGG     420
```

```
AGGTTCATCC ATGTTWGGAC TCTTTGTGGA ACATGGGCCT TATGTTGTCA CAAGTAACAT      480

GACCTTGCGT GACAGAGACT TCCCCTGGAC CACAACGSTC TCCATGCTTT ACATTGACAA      540

TCCAGTGGGC ACAGGCTTCA GTTTTACTGA TGATACCCAC GGATATGCAG TCAATGAGGA      600

CGATGTAGCA CGGGATTTAT ACAGTGCACT AATTCAGTTT TTCCAGATAT TTCCTGAATA      660

TAAAAATAAT GACTTTTATG TCACTGGGGA GTCTTATGCA GGGAAATATG TGCCAGCCAT      720

TGCACACCTC ATCCATTCCC TCAACCCTGT GAGAGAGGTG AAGATCAACC TGAACGGAAT      780

TGCTATTGGA GATGGATATT CTGATCCCGA ATCAATTATA GGGGGCTATG CAGAATTCCT      840

GTACCAAATT GGCTTGTTGG ATGAGAAGCA AAAAAAGTAC TTCCAGAAGC AGTGCCATGA      900

ATGCATAGAA CACATCAGGA AGCAGAACTG GTTTGAGGCC TTTGAAATAC TGGATAAACT      960

ACTAGATGGC GACTTAACAA GTGATCCTTC TTACTTCCAG AATGTTACAG GATGTAGTAA     1020

TTACTATAAC TTTTTGCGGT GCACGGAACC TGAGGATCGA CTTTACTATG TGAAATTTTT     1080

GTCACTCCCA GAGGTGAGAC AAGCCATCCA CGTGGGGAAT CAGACTTTTA ATGATGGAAC     1140

TATAGTTGAA AAGTACTTGC GAGAAGATAC AGTACAGTCA GTTAAGCCAT GGTTAACTGA     1200

AATCATGAAT AATTATAAGG TTCTGATCTA CAATGGCCAA CTGGACATCA TCGTGGCAGC     1260

TGCCCTGACA GAGCGCTCCT TGATGGGCAT GGACTGGAAA GGTTCCCAGG AATACAAGAA     1320

GGCAGAAAAA AAAGTTTGGA AGATCTTTAA ATCTGACAGT GAAGTGGCTG GTTACATCCG     1380

GCAAGTGGGT GACTTCCATC AGGTAATTAT TCGAGGTGGA GGACATATTT TACCCTATGA     1440

CCAGCCTCTG AGAGCTTTTG ACATGATTAA TCGATTCATT TATGGAAAAG GATGGGATCC     1500

TTATGTTGGA TAAACTACCT TCCCAAAAGA GAACATCAGA GGTTTTCATN T             1551

(2) INFORMATION FOR SEQ ID NO:5:

(i) SEQUENCE CHARACTERISTICS:
        (A) LENGTH: 351 amino acids
        (B) TYPE: amino acid
        (C) STRANDEDNESS: single
        (D) TOPOLOGY: linear (vii) IMMEDIATE SOURCE:
        (A) LIBRARY: COLNCRT01
        (B) CLONE: 770469

(xi) SEQUENCE DESCRIPTION: SEQ ID NO:5:

Met Val Gly Ala Met Trp Lys Val Ile Val Ser Leu Val Leu Leu Met
 1               5                  10                  15

Pro Gly Pro Cys Gly Gly Leu Phe His Ser Leu Tyr Arg Ser Val Ser
            20                  25                  30

Met Pro Pro Lys Gly Asp Ser Gly Gln Pro Leu Phe Leu Thr Pro Tyr
        35                  40                  45

Ile Glu Ala Gly Lys Ile Tyr Thr Gly Thr Asn Ser Val Phe Gln Ile
    50                  55                  60

Phe Pro Glu Tyr Lys Asn Asn Asp Phe Tyr Val Thr Gly Glu Ser Tyr
65                  70                  75                  80

Ala Gly Lys Tyr Val Pro Ala Ile Ala His Leu Ile His Ser Leu Asn
                85                  90                  95

Pro Val Arg Glu Val Lys Ile Asn Leu Asn Gly Ile Ala Ile Gly Asp
            100                 105                 110

Gly Tyr Ser Asp Pro Glu Ser Ile Ile Gly Gly Tyr Ala Glu Phe Leu
        115                 120                 125

Tyr Gln Ile Gly Leu Leu Asp Glu Lys Gln Lys Lys Tyr Phe Gln Lys
```

```
             130                 135                 140
Gln Cys His Glu Cys Ile Glu His Ile Arg Lys Gln Asn Trp Phe Glu
145                 150                 155                 160
Ala Phe Glu Ile Leu Asp Lys Leu Leu Asp Gly Asp Leu Thr Ser Asp
                165                 170                 175
Pro Ser Tyr Phe Gln Asn Val Thr Gly Cys Ser Asn Tyr Tyr Asn Phe
                180                 185                 190
Leu Arg Cys Thr Glu Pro Glu Asp Gln Leu Tyr Tyr Val Lys Phe Leu
                195                 200                 205
Ser Leu Pro Glu Val Arg Gln Ala Ile His Val Gly Asn Gln Thr Phe
                210                 215                 220
Asn Asp Gly Thr Ile Val Glu Lys Tyr Leu Arg Glu Asp Thr Val Gln
225                 230                 235                 240
Ser Val Lys Pro Trp Leu Thr Glu Ile Met Asn Asn Tyr Lys Val Leu
                245                 250                 255
Ile Tyr Asn Gly Gln Leu Asp Ile Ile Val Ala Ala Leu Thr Glu
                260                 265                 270
Arg Ser Leu Met Gly Met Asp Trp Lys Gly Ser Gln Glu Tyr Lys Lys
                275                 280                 285
Ala Glu Lys Lys Val Trp Lys Ile Phe Lys Ser Asp Ser Glu Val Ala
290                 295                 300
Gly Tyr Ile Arg Gln Val Gly Asp Phe His Gln Val Ile Ile Arg Gly
305                 310                 315                 320
Gly Gly His Ile Leu Pro Tyr Asp Gln Pro Leu Arg Ala Phe Asp Met
                325                 330                 335
Ile Asn Arg Phe Ile Tyr Gly Lys Gly Trp Asp Pro Tyr Val Gly
                340                 345                 350

(2) INFORMATION FOR SEQ ID NO:6:

(i) SEQUENCE CHARACTERISTICS:
        (A) LENGTH: 1263 base pairs
        (B) TYPE: nucleic acid
        (C) STRANDEDNESS: single
        (D) TOPOLOGY: linear (vii) IMMEDIATE SOURCE:
        (A) LIBRARY: COLNCRT01
        (B) CLONE: 770469

(xi) SEQUENCE DESCRIPTION: SEQ ID NO:6:

AAGGCAAACC GGCTGGGGTC CTTGCGCGCC GCGGCTCAGG GAGGAGCACC GACTGCCCCG    60

CACCCTGAGA GATGGTTGGT GCCATGTGGA AGGTGATTGT TTCGCTGGTC CTGTTGATGC   120

CTGGCCCCTG TGGTGGGCTG TTTCACTCCC TATACAGAAG TGTTTCCATG CCACCTAAGG   180

GAGACTCAGG ACAGCCATTA TTTCTCACCC CTTACATTGA AGCTGGGAAG ATTTATACAG   240

GCACTAATTC AGTTTTCCAG ATATTTCCTG AATATAAAAA TAATGACTTT TATGTCACTG   300

GGGAGTCTTA TGCAGGGAAA TATGTGCCAG CCATTGCACA CCTCATCCAT TCCCTCAACC   360

CTGTGAGAGA GGTGAAGATC AACCTGAACG GAATTGCTAT TGGAGATGGA TATTCTGATC   420

CCGAATCAAT TATAGGGGGC TATGCAGAAT TCCTGTACCA AATTGGCTTG TTGGATGAGA   480

AGCAAAAAAA GTACTTCCAG AAGCAGTGCC ATGAATGCAT AGAACACATC AGGAAGCAGA   540

ACTGGTTTGA GGCCTTTGAA ATACTGGATA AACTACTAGA TGGCGACTTA CAAGTGATC   600

CTTCTTACTT CCAGAATGTT ACAGGATGTA GTAATTACTA TAACTTTTTG CGGTGCACGG   660

AACCTGAGGA TCAGCTTTAC TATGTGAAAT TTTTGTCACT CCCAGAGGTG AGACAAGCCA   720
```

```
TCCACGTGGG GAATCAGACT TTTAATGATG GAACTATAGT TGAAAAGTAC TTGCGAGAAG      780

ATACAGTACA GTCAGTTAAG CCATGGTTAA CTGAAATCAT GAATAATTAT AAGGTTCTGA      840

TCTACAATGG CCAACTGGAC ATCATCGTGG CAGCTGCCCT GACAGAGCGC TCCTTGATGG      900

GCATGGACTG GAAAGGATCC CAGGAATACA AGAAGGCAGA AAAAAAAGTT TGGAAGATCT      960

TTAAATCTGA CAGTGAAGTG GCTGGTTACA TCCGGCAAGT GGGTGACTTC CATCAGGTAA     1020

TTATTCGAGG TGGAGGACAT ATTTTACCCT ATGACCAGCC TCTGAGAGCT TTTGACATGA     1080

TTAATCGATT CATTTATGGA AAAGGATGGG ATCCTTATGT TGGATAAACT ACCTTCCCAA     1140

AAGAGAACAT CAGAGGTTTT CATTGCTGAA AAGAAAATCG TAAAAACAGA AAATGTCATA     1200

GGAATAAAAA AATTATCTTT TCATATCTGC AAGATTTTTT TCATCAATAA AAATTATCCT     1260

TGA                                                                  1263

(2) INFORMATION FOR SEQ ID NO:7:

(i) SEQUENCE CHARACTERISTICS:
        (A) LENGTH: 471 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1718107

(xi) SEQUENCE DESCRIPTION: SEQ ID NO:7:

Met Val Lys Phe His Leu Leu Val Leu Ile Ala Phe Thr Cys Tyr Thr
 1               5                  10                  15

Cys Ser Asp Ala Thr Leu Trp Asn Pro Tyr Lys Lys Leu Met Arg Gly
            20                  25                  30

Ser Ala Ser Pro Pro Arg Pro Gly Glu Ser Gly Glu Pro Leu Phe Leu
        35                  40                  45

Thr Pro Leu Leu Gln Asp Gly Lys Ile Glu Glu Ala Arg Asn Lys Ala
    50                  55                  60

Arg Val Asn His Pro Met Leu Ser Ser Val Glu Ser Tyr Ser Gly Phe
65                  70                  75                  80

Met Thr Val Asp Ala Lys His Asn Ser Asn Leu Phe Phe Trp Tyr Val
                85                  90                  95

Pro Ala Lys Asn Asn Arg Glu Gln Ala Pro Ile Leu Val Trp Leu Gln
            100                 105                 110

Gly Gly Pro Gly Ala Ser Ser Leu Phe Gly Met Phe Glu Glu Asn Gly
        115                 120                 125

Pro Phe His Ile His Arg Asn Lys Ser Val Lys Gln Arg Glu Tyr Ser
    130                 135                 140

Trp His Gln Asn His His Met Ile Tyr Ile Asp Asn Pro Val Gly Thr
145                 150                 155                 160

Gly Phe Ser Phe Thr Asp Ser Asp Glu Gly Tyr Ser Thr Asn Glu Glu
                165                 170                 175

His Val Gly Glu Asn Leu Met Lys Phe Ile Gln Gln Phe Phe Val Leu
            180                 185                 190

Phe Pro Asn Leu Leu Lys His Pro Phe Tyr Ile Ser Gly Glu Ser Tyr
        195                 200                 205

Gly Gly Lys Phe Val Pro Ala Phe Gly Tyr Ala Ile His Asn Ser Gln
    210                 215                 220

Ser Gln Pro Lys Ile Asn Leu Gln Gly Leu Ala Ile Gly Asp Gly Tyr
```

```
                       225                 230                 235                 240
Thr Asp Pro Leu Asn Gln Leu Asn Tyr Gly Glu Tyr Leu Tyr Glu Leu
                245                 250                 255

Gly Leu Ile Asp Leu Asn Gly Arg Lys Lys Phe Asp Glu Asp Thr Ala
                260                 265                 270

Ala Ala Ile Ala Cys Ala Glu Arg Lys Asp Met Asn Ser Ala Asn Arg
                275                 280                 285

Leu Ile Gln Gly Leu Phe Asp Gly Leu Asp Gly Gln Glu Ser Tyr Phe
            290                 295                 300

Lys Lys Val Thr Gly Phe Ser Ser Tyr Tyr Asn Phe Ile Lys Gly Asp
305                 310                 315                 320

Glu Glu Ser Lys Gln Asp Ser Val Leu Met Glu Phe Leu Ser Asn Pro
                325                 330                 335

Glu Val Arg Lys Gly Ile His Val Gly Glu Leu Pro Phe His Asp Ser
                340                 345                 350

Asp Gly His Asn Lys Val Ala Glu Met Leu Ser Glu Asp Thr Leu Asp
            355                 360                 365

Thr Val Ala Pro Trp Val Ser Lys Leu Leu Ser His Tyr Arg Val Leu
        370                 375                 380

Phe Tyr Asn Gly Gln Leu Asp Ile Ile Cys Ala Tyr Pro Met Thr Val
385                 390                 395                 400

Asp Phe Leu Met Lys Met Pro Phe Asp Gly Asp Ser Glu Tyr Lys Arg
                405                 410                 415

Ala Asn Arg Glu Ile Tyr Arg Val Asp Gly Glu Ile Ala Gly Tyr Lys
                420                 425                 430

Lys Arg Ala Gly Arg Leu Gln Glu Val Leu Ile Arg Asn Ala Gly His
                435                 440                 445

Met Val Pro Arg Asp Gln Pro Lys Trp Ala Phe Asp Met Ile Thr Ser
        450                 455                 460

Phe Thr His Lys Asn Tyr Leu
465                 470

(2) INFORMATION FOR SEQ ID NO:8:

(i) SEQUENCE CHARACTERISTICS:
        (A) LENGTH: 480 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 190283

(xi) SEQUENCE DESCRIPTION: SEQ ID NO:8:

Met Ile Arg Ala Ala Pro Pro Leu Phe Leu Leu Leu Leu Leu
1               5                   10                  15

Leu Leu Leu Val Ser Trp Ala Ser Arg Gly Glu Ala Ala Pro Asp Gln
                20                  25                  30

Asp Glu Ile Gln Arg Leu Pro Gly Leu Ala Lys Gln Pro Ser Phe Arg
            35                  40                  45

Gln Tyr Ser Gly Tyr Leu Lys Ser Ser Gly Ser Lys His Leu His Tyr
        50                  55                  60

Trp Phe Val Glu Ser Gln Lys Asp Pro Glu Asn Ser Pro Val Val Leu
65                  70                  75                  80

Trp Leu Asn Gly Gly Pro Gly Cys Ser Ser Leu Asp Gly Leu Leu Thr
                85                  90                  95
```

```
Glu His Gly Pro Phe Leu Val Gln Pro Asp Gly Val Thr Leu Glu Tyr
            100                 105                 110

Asn Pro Tyr Ser Trp Asn Leu Ile Ala Asn Val Leu Tyr Leu Glu Ser
        115                 120                 125

Pro Ala Gly Val Gly Phe Ser Tyr Ser Asp Asp Lys Phe Tyr Ala Thr
    130                 135                 140

Asn Asp Thr Glu Val Ala Gln Ser Asn Phe Glu Ala Leu Gln Asp Phe
145                 150                 155                 160

Phe Arg Leu Phe Pro Glu Tyr Lys Asn Asn Lys Leu Phe Leu Thr Gly
                165                 170                 175

Glu Ser Tyr Ala Gly Ile Tyr Ile Pro Thr Leu Ala Val Leu Val Met
            180                 185                 190

Gln Asp Pro Ser Met Asn Leu Gln Gly Leu Ala Val Gly Asn Gly Leu
        195                 200                 205

Ser Ser Tyr Glu Gln Asn Asp Asn Ser Leu Val Tyr Phe Ala Tyr Tyr
    210                 215                 220

His Gly Leu Leu Gly Asn Arg Leu Trp Ser Ser Leu Gln Thr His Cys
225                 230                 235                 240

Cys Ser Gln Asn Lys Cys Asn Phe Tyr Asp Asn Lys Asp Leu Glu Cys
                245                 250                 255

Val Thr Asn Leu Gln Glu Val Ala Arg Ile Val Gly Asn Ser Gly Leu
            260                 265                 270

Asn Ile Tyr Asn Leu Tyr Ala Pro Cys Ala Gly Gly Val Pro Ser His
        275                 280                 285

Phe Arg Tyr Glu Lys Asp Thr Val Val Gln Asp Leu Gly Asn Ile
    290                 295                 300

Phe Thr Arg Leu Pro Leu Lys Arg Met Trp His Gln Ala Leu Leu Arg
305                 310                 315                 320

Ser Gly Asp Lys Val Arg Met Asp Pro Pro Cys Thr Asn Thr Thr Ala
                325                 330                 335

Ala Ser Thr Tyr Leu Asn Asn Pro Tyr Val Arg Lys Ala Leu Asn Ile
            340                 345                 350

Pro Glu Gln Leu Pro Gln Trp Asp Met Cys Asn Phe Leu Val Asn Leu
        355                 360                 365

Gln Tyr Arg Arg Leu Tyr Arg Ser Met Asn Ser Gln Tyr Leu Lys Leu
    370                 375                 380

Leu Ser Ser Gln Lys Tyr Gln Ile Leu Leu Tyr Asn Gly Asp Val Asp
385                 390                 395                 400

Met Ala Cys Asn Phe Met Gly Asp Glu Trp Phe Val Asp Ser Leu Asn
                405                 410                 415

Gln Lys Met Glu Val Gln Arg Arg Pro Trp Leu Val Lys Tyr Gly Asp
            420                 425                 430

Ser Gly Glu Gln Ile Ala Gly Phe Val Lys Glu Phe Ser His Ile Ala
        435                 440                 445

Phe Leu Thr Ile Lys Gly Ala Gly His Met Val Pro Thr Asp Lys Pro
    450                 455                 460

Leu Ala Ala Phe Thr Met Phe Ser Arg Phe Leu Asn Lys Gln Pro Tyr
465                 470                 475                 480
```

HUMAN SERINE CARBOXYPEPTIDASE

This application is a divisional application of U.S. application Ser. No. 08/828,488, filed Mar. 31, 1997 now U.S. Pat. No. 5,925,521.

FIELD OF THE INVENTION

This invention relates to nucleic acid and amino acid sequences of a novel human serine carboxypeptidase and to the use of these sequences in the diagnosis, prevention, and treatment of disorders associated with expression of serine carboxypeptidase.

BACKGROUND OF THE INVENTION

Serine carboxypeptidases are a family of proteases found in vertebrate and invertebrate tissues that function in many physiological processes. These proteases remove a wide range of COOH-terminal amino acids, and in doing so are able to activate, inactivate, and modulate enzyme and peptide hormone activity. Many active forms of mammalian carboxypeptidases are located in lysosomes where they regulate intracellular protein processing, degradation and turnover. In plants and insects the serine carboxypeptidases play a role in posttranslational protein modifications including mobilization of storage proteins and hormone activation. The extensively characterized KEX1 yeast carboxypeptidase activates K1 and K2 killer toxins and alpha-factor (mating pheromone) by removing the lysine and arginine residues from the precursor forms. The carboxypeptidases exhibiting this enzymatic activity are distinguished by a common catalytic triad, Ser, His, and Asp residues, and are inhibited by serpins (Galjart, J. (1988) Cell 54: 755–764; Latchinian-Sadek, L. et al. (1994) Eur. J. Biochem. 219: 647–652; Elsliger, M. A. (1994) Proteins 18: 81–93).

Human lysosomal protective protein (HPP) is a serine carboxypeptidase with multiple biological properties. It functions as a protease with properties similar to cathepsin A at the acidic pH of lysosomes, and as an esterase or a carboxyl-terminal deamidase at neutral pH. HPP is similar to serine carboxypeptidases derived from insects, yeast and plants that are implicated in proteolytic activation of a number of enzymes or other biologically active molecules. It is synthesized as a 54-kDa precursor and can be processed into a catalytically active disulfide-linked 32 and 20-kDa heterodimer. The precursor dimerizes at neutral pH shortly after synthesis and is transported to the lysosome. The human enzyme, purified from platelets and lymphocytes, functions both in vitro and in vivo to inactivate selected signaling peptides, including substance P, oxytocin, netiropeptides, and endothelin I (Galjart, J., supra; Jackman, H. L. (1990) J. Biol. Chem. 265:11265–11272).

HPP is designated as 'protective protein' when it forms a complex with lysosomal glycosidases, β-D- galactosidase and N-acetyl-neuramidase (sialidase), and protects them from degradation. Complex formation serves to regulate enzyme activity within the lysosomes. An inherited metabolic disease, galactosialidosis, is caused by a genetic defect of in HPP, which results in a deficiency of lysosomal glycosidase activities. When the hydrolytic activity of these lysosomal glycosidases is compromised, heterogeneous neurosomatic manifestations result. Several HPP mutations have been identified for each clinical subtype, and a correlation has been shown between genotype and phenotype (Shimmoto, M., et al.(1993) J. Clin. Invest. 91: 2393–2398).

The vitellins, multisubunit phosphoglycoproteins, are stored in yolk granules and serve as a primary nutrient source for developing embryos. The vitellogenic carboxypeptidase, (VCP), hydrolyzes yolk proteins for utilization by the embryo during development. In mosquito (*Aedes aegypti*), VCP proenzyme is produced in extraovarian tissues, secreted into the hemolymph, and selectively internalized by developing oocytes where it is accumulated in yolk bodies. It is activated at the onset of embryogenesis and is completely degraded by the time the first instar larvae hatch (Cho, W. L., et al. (1991) Proc. Natl. Acad.Sci. 88: 10821–10824).

The discovery of proteins related to human lysosomal protective protein and *Aedes aegypti* vitellogenic carboxypeptidase and the polynucleotides encoding them satisfies a need in the art by providing new compositions useful in the diagnosis and treatment of disorders associated with expression of serine carboxypeptidases.

SUMMARY OF THE INVENTION

The present invention features a novel human serine carboxypeptidase hereinafter designated CPEPT and characterized as having similarity to human lysosomal protective protein (HPP) and *Aedes aegypti* vitellogenic carboxypeptidase(VCP). Accordingly, the invention features a substantially purified CPEPT having the amino acid sequence shown in SEQ ID NO:1. The invention also features a polypeptide variant of CPEPT, SEQ ID NO:3, where $D_{76}$ is replaced by G, $E_{111}$ is replaced by G, $K_{418}$ is removed, $G_{428}$ is replaced by E, and $T_{450}$ is replaced by I. In addition, the invention features a potential splice variant of CPEPT, SEQ ID NO:5, where $D_{21}$ is replaced by G, residues $Q_{55}$ through $F_{86}$ are replaced by YTGTNSV, $K_{418}$ is removed, $G_{428}$ is replaced by E, and $T_{450}$ is replaced by I.

The invention also features isolated and substantially purified polynucleotides that encode CPEPT, and the CPEPT variants (SEQ ID NO:2, SEQ ID NO:4, and SEQ ID NO:6)

The invention also features a substantially purified CPEPT potential splice variant having the amino acid sequence shown in SEQ ID NO:5.

The invention also features polynucleotide sequences comprising the complement of SEQ ID NO:2, SEQ ID NO:4, and SEQ ID NO 6 or variants thereof In addition, the invention features polynucleotide sequences which hybridize under stringent conditions to SEQ ID NO:2, SEQ ID NO:4, and SEQ ID NO:6.

The invention additionally features expression vectors and host cells comprising polynucleotides that encode CPEPT and in particular those polynucleotides having SEQ ID NO:2, SEQ ID NO:4, or SEQ ID NO:6. The invention also features antibodies which bind specifically to CPEPT, and pharmaceutical compositions comprising substantially purified CPEPT. The invention also features agonists and antagonists of CPEPT. The invention also features a method for treating disorders associated with decreased serine carboxypeptidase levels by administering CPEPT and a method for treating disorders associated with increased serine carboxypeptidase levels by administering an antagonist to CPEPT.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of CPEPT. The alignment was produced using MACDNASIS PRO® software (Hitachi Software Engineering Co., Ltd., San Bruno, Calif.).

Figure 2B:
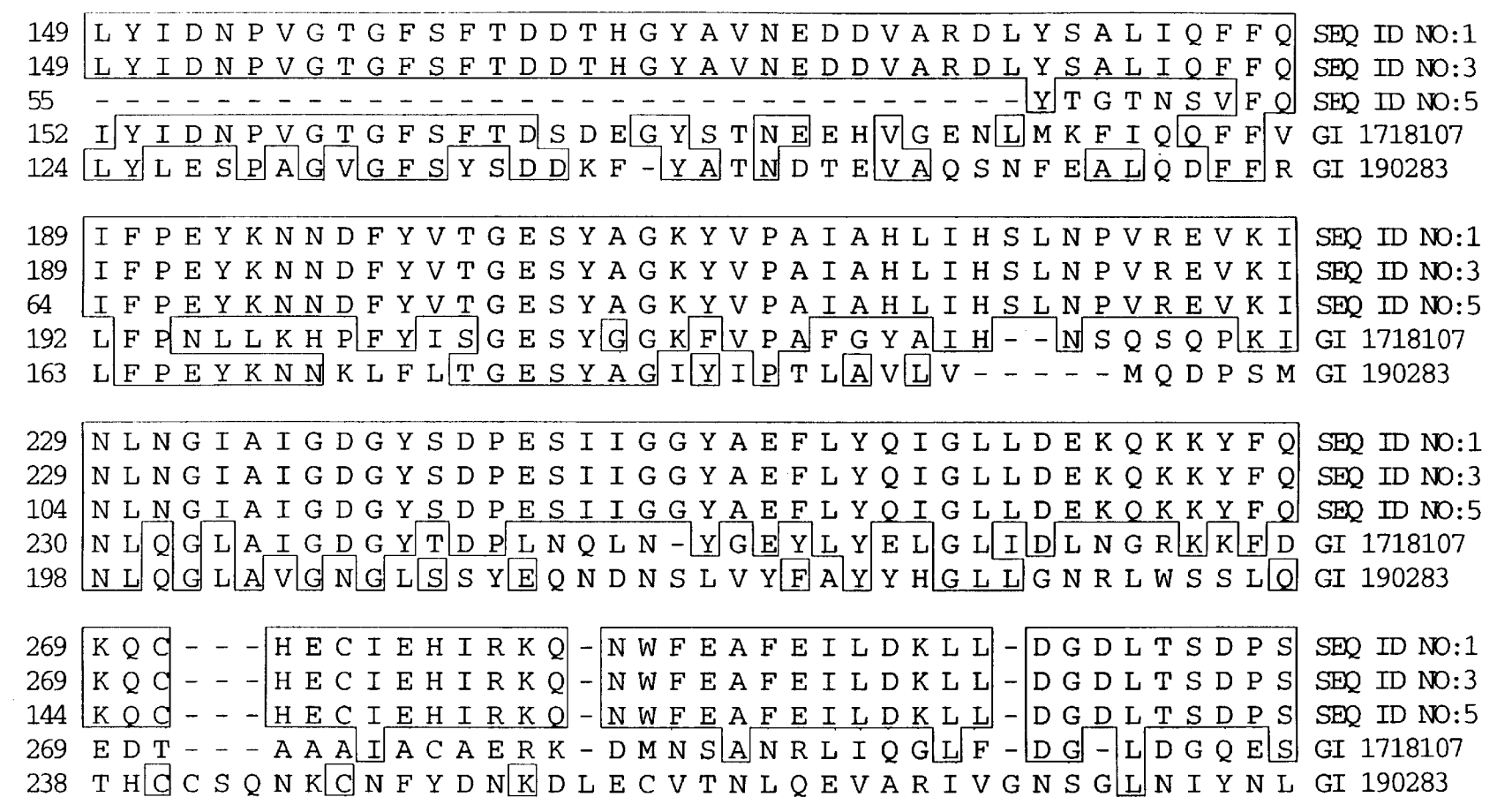

FIGS. 2A, 2B, 2C, and 2D show the amino acid sequence alignments among SEQ ID NO:1, SEQ ID NO:3, SEQ ID NO:5, GI 1718107 (SEQ ID NO:7), and GI 190283 (SEQ ID NO:8). The alignment was produced using the multisequence alignment program of DNASTAR software (DNASTAR Inc., Madison, Wis.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

CPEPT, as used herein, refers to the amino acid sequences of substantially purified CPEPT obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of CPEPT, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic CPEPT, or any oligopeptide thereof, to induce a specific immune response in appropriate animals or cells and to bind with specific antibodies.

The term "agonist", as used herein, refers to a molecule which, when bound to CPEPT, causes a change in CPEPT which modulates the activity of CPEPT. Agonists may include proteins, nucleic acids, carbohydrates, or any other molecules which bind to CPEPT.

The terms "antagonist" or "inhibitor", as used herein, refer to a molecule which, when bound to CPEPT, blocks or modulates the biological or immunological activity of CPEPT. Antagonists and inhibitors may include proteins, nucleic acids, carbohydrates, or any other molecules which bind to CPEPT.

The term "modulate", as used herein, refers to a change or an alteration in the biological activity of CPEPT. Modulation may be an increase or a decrease in protein activity, a change in binding characteristics, or any other change in the biological, functional or immunological properties of CPEPT.

The term "mimetic", as used herein, refers to a molecule, the structure of which is developed from knowledge of the structure of CPEPT or portions thereof and, as such, is able to effect some or all of the actions of CPEPT-like molecules.

The term "derivative", as used herein, refers to the chemical modification of a nucleic acid encoding CPEPT or the encoded CPEPT. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acid strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human CPEPT and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding CPEPT or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding CPEPT in a sample and thereby correlates with expression of the transcript from the polynucleotide encoding the protein.

"Alterations" in the polynucleotide of SEQ ID NO:2, as used herein, comprise any alteration in the sequence of polynucleotides encoding CPEPT including deletions, insertions, and point mutations that may be detected using hybridization assays. Included within this definition is the detection of alterations to the genomic DNA sequence which encodes CPEPT (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding CPEPT (e.g., using fluorescent in situ hybridization [FISH] to metaphase chromosomes spreads).

As used herein, the term "antibody" refers to intact molecules as well as fragments thereof, such as Fab F(ab')$_2$, and Fv, which are capable of binding the epitopic determinant. Antibodies that bind CPEPT polypeptides can be prepared using intact polypeptides or fragments containing small peptides of interest as the immunizing antigen. The polypeptide or oligopeptide used to immunize an animal can be derived from the translation of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human serine carboxypeptidase, (CPEPT) and two variants of CPEPT, collectively referred to as CPEPT, the polynucleotides encoding CPEPT, and the use of these compositions for the diagnosis, prevention, or treatment of disorders associated with expression of CPEPT.

Nucleic acids encoding the human CPEPT of the present invention were first identified in Incyte Clone 443004 from the macrophage cDNA library (MPHGNOT03) through a computer-generated search for amino acid sequence alignments. SEQ ID NO:2 was derived from extension of the nucleic acid sequence of Incyte Clone 443004.

Nucleic acids encoding the human CPEPT variant of the present invention were first identified in Incyte Clone 566993 from the macrophage cell cDNA library (MMLR3DT01) through a computer-generated search for amino acid sequence alignments. SEQ ID NO:4, was derived from extension and assembly of the nucleic acid sequence of Incyte Clone 566993.

Nucleic acids encoding the human CPEPT potential splice variant of the present invention were first identified in Incyte Clone 770469 from the colon cDNA library (COLNCRT01) through a computer-generated search for amino acid sequence alignments.

SEQ ID NO:6 was derived from extension of the nucleic acid sequences of Incyte Clone 770469.

In one embodiment, the invention encompasses a polypeptide comprising the amino acid sequence of SEQ ID NO:1, as shown in FIGS. 1A through 1E. CPEPT is 477 amino acids in length. CPEPT has chemical and structural homology with VCP (GI 1718107; SEQ ID NO:7) and HPP (GI 190283, SEQ ID NO:8). In particular, CPEPT, VCP, and HPP share 42% and 28% identity, respectively. Additionally, CPEPT, VCP, and HPP contain the S, D, and H residues of the serine carboxypeptidase catalytic triad at $S_{189}$, $D_{351}$, and $H_{448}$ (CPEPT), $S_{189}$, $D_{351}$, and $H_{448}$ (VCP), and $S_{79}$, $D_{226}$, and $H_{323}$ (HPP).

The invention also encompasses CPEPT variants. A preferred CPEPT variant is one having about 28%, and more preferably 42%, amino acid sequence identity to the CPEPT amino acid sequence (SEQ ID NO:1). Two particular variants are SEQ ID NO:3 and SEQ ID NO:5.

The invention also encompasses polynucleotides which encode CPEPT. Accordingly, any nucleic acid sequence which encodes the amino acid sequence of CPEPT and variants thereof can be used to generate recombinant molecules which express CPEPT. In a particular embodiment, the invention encompasses a polynucleotide comprising the nucleic acid sequence of SEQ ID NO:2, SEQ ID NO:4, or SEQ ID NO:6.

It will be appreciated by those skilled in the art that as a result of the degeneracy of the genetic code, a multitude of nucleotide sequences encoding CPEPT, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring CPEPT, and all such variations are to be considered as being specifically disclosed.

Although nucleotide sequences which encode CPEPT and its variants are preferably capable of hybridizing to the nucleotide sequence of the naturally occurring CPEPT under appropriately selected conditions of stringency, it may be advantageous to produce nucleotide sequences encoding CPEPT or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CPEPT and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode CPEPT and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding CPEPT or any portion thereof.

Also encompassed by the invention are polynucleotide sequences that are capable of hybridizing to the claimed nucleotide sequences, and in particular, those shown in SEQ ID NO:2, SEQ ID NO:4, and SEQ ID NO:6 under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding CPEPT which are encompassed by the invention include deletions, insertions, or substitutions of different nucleotides resulting in a polynucleotide that encodes the same or a functionally equivalent CPEPT. The encoded protein may also contain deletions, insertions, or substitutions of amino acid residues which produce a silent change and result in a functionally equivalent CPRPT. Deliberate amino acid substitutions may be made on the basis of similarity in polarity, charge, solubility, hydrophobicity, hydrophilicity, and/or the amphipathic nature of the residues as long as the biological activity of CPEPT is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding CPEPT. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI 377 DNA sequencers (Perkin Elmer).

The nucleic acid sequences encoding CPEPT may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode CPEPT, or fusion proteins or functional equivalents thereof, may be used in recombinant DNA molecules to direct expression of CPEPT in appropriate host cells. Due to the inherent degeneracy of the genetic code, other DNA sequences which encode substantially the same or a functionally equivalent amino acid sequence may be produced and these sequences may be used to clone and express CPEPT.

As will be understood by those of skill in the art, it may be advantageous to produce CPEPT-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter CPEPT encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding CPEPT may be ligated to a heterologous sequence to encode a fusion protein. For example, to screen peptide libraries for inhibitors of CPEPT activity, it may be useful to encode a chimeric CPEPT protein that can be recognized by a commercially available antibody. A fusion protein may also be engineered to contain a cleavage site located between the CPEPT encoding sequence and the heterologous protein sequence, so that CPEPT may be cleaved and purified away from the heterologous moiety.

In another embodiment, sequences encoding CPEPT may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of CPEPT, or a portion thereof. For example, peptide synthesis can be performed using various solid-phase techniques (Roberge, J. Y. et al. (1995) Science 269:202–204) and automated synthesis may be achieved, for example, using the ABI 431 A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of CPEPT, or any part thereof, may be altered during direct synthesis and/or combined using chemical methods with sequences from other proteins, or any part thereof, to produce a variant polypeptide.

In order to express a biologically active CPEPT, the nucleotide sequences encoding CPEPT or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding CPEPT and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding CPEPT. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding CPEPT, vectors based on SV40 or EBV may be used with an appropriate selectable marker.

In bacterial systems, a number of expression vectors may be selected depending upon the use intended for CPEPT. For example, when large quantities of CPEPT are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding CPEPT may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding CPEPT may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express CPEPT. For example, in one such system, *Autographa californica* nuclear polyhedrosis virus (AcNPV) is used as a vector to express foreign genes in *Spodoptera frugiperda* cells or in Trichoplusia larvae. The sequences encoding CPEPT may be cloned into a non-essential region of the virus, such as the polyhedrin gene, and placed under control of the polyhedrin promoter. Successful insertion of CPEPT will render the polyhedrin gene inactive and produce recombinant virus lacking coat protein. The recombinant viruses may then be used to infect, for example, *S. frugiperda* cells or Trichoplusia larvae in which CPEPT may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding CPEPT may be ligated into an adenovirus transcription/translation complex consisting of the late promoter and tripartite leader sequence. Insertion in a non-essential E1 or E3 region of the viral genome may be used to obtain a viable virus which is capable of expressing CPEPT in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding CPEPT. Such signals include the ATG initiation codon and adjacent sequences. In cases where sequences encoding CPEPT, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express CPEPT may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1998) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding CPEPT is inserted within a marker gene sequence, recombinant cells containing sequences encoding CPEPT can be identified by the absence of marker gene function. Alternatively, a marker gene can be placed in tandem with a sequence encoding CPEPT under the control of a single promoter. Expression of the marker gene in response to induction or selection usually indicates expression of the tandem gene as well.

Alternatively, host cells which contain the nucleic acid sequence encoding CPEPT and express CPEPT may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding CPEPT can be detected by DNA-DNA or DNA-RNA hybridization or amplification using probes or portions or fragments of polynucleotides encoding CPEPT. Nucleic acid amplification based assays involve the use of oligonucleotides or oligomers based on the sequences encoding CPEPT to detect transformants containing DNA or RNA encoding CPEPT. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of CPEPT, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on CPEPT is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding CPEPT include oligolabeling, nick translation, end-labeling or PCR amplification using a labeled nucleotide. Alternatively, the sequences encoding CPEPT, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding CPEPT may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode CPEPT may be designed to contain signal sequences which direct secretion of CPEPT through a prokaryotic or eukaryotic cell membrane. Other recombinant constructions may be used to join sequences encoding CPEPT to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and CPEPT may be used to facilitate purification. One such expression vector provides for expression of a fusion protein containing CPEPT and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying CPEPT from the fusion protein. A discussion of vectors which contain fusion proteins is provided in Kroll, D. J. et al. (1993; DNA Cell Biol. 12:441–453).

In addition to recombinant production, fragments of CPEPT may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using an Applied Biosystems 431A peptide sythesizer (Perkin Elmer). Various fragments of CPEPT may be chemically synthesized separately and combined using chemical methods to produce the full length molecule.

Therapeutics

Based on the chemical and structural homology among CPEPT (SEQ ID NO:1), VCP (SEQ ID NO:7), and HPP (SEQ ID NO:8), CPEPT appears to play a role in the activation of enzymes including β-D-galactosidase and N-acetyl-neuramidase and in the deactivation of signaling peptides including substance P, oxytocin, neuropeptides, and endothelin I.

Therefore, in one embodiment, CPEPT or a fragment or derivative thereof may be administered to a subject to treat or prevent disorders related to decreased expression of CPEPT. Such conditions and disorders may include, but are not limited to, diabetes mellitus, galactosialidosis, inflammatory glomerulonephritis, ischemic renal failure, cyclosporine toxicity, endotoxemia, rhabdomyolysis, extracellular matrix accumulation, fibrosis, hypertension, atherosclerosis, coronary vasoconstriction, and ischemic heart disease.

In another embodiment, a vector capable of expressing CPEPT, or a fragment or a derivative thereof, may also be administered to a subject to treat the disorders listed above.

In another embodiment, antagonists or inhibitors of CPEPT may be administered to a subject to treat or prevent disorders associated with increased CPEPT expression. Such conditions and disorders may include, but are not limited to, fibrosis, lesions occurring in brain disorders such as stroke, trauma, infarcts, progressive multifocal leukoencephalopathy, subacute sclerosing panencephalitis, Alzheimer's disease, Binswanger's disease, Huntington's disease, Parkinson's disease, epilepsy, dementia, multiple sclerosis, neurofibromatosis, and amyotrophic lateral sclerosis. In one aspect, antibodies which are specific for CPEPT may be used directly as an antagonist, or indirectly as a targeting or delivery mechanism for bringing a pharmaceutical agent to cells or tissue which express CPEPT.

In another embodiment, a vector expressing antisense or complement of the polynucleotide encoding CPEPT may be administered to a subject to treat or prevent the disorders listed above.

In other embodiments, any of the therapeutic proteins, antagonists, antibodies, agonists, antisense or complement sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of CPEPT may be produced using methods which are generally known in the art. In particular, purified CPEPT may be used to produce antibodies or to screen libraries of pharmaceutical agents to identify those which specifically bind CPEPT.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with CPEPT or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to CPEPT have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of CPEPT amino acids may be fused with those of another protein such as keyhole limpet hemocyanin and antibody produced against the chimeric molecule.

Monoclonal antibodies to CPEPT may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce CPEPT-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for CPEPT may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CPEPT and its specific antibody. A two-site, monoclonal-based immunoassay utilizing monoclonal antibodies reactive to two non-interfering CPEPT epitopes is preferred, but a competitive binding assay may also be employed (Maddox, supra).

In another embodiment of the invention, the polynucleotides encoding CPEPT, or any fragment thereof, or antisense molecules, may be used for therapeutic purposes. In one aspect, antisense to the polynucleotide encoding CPEPT may be used in situations in which it would be desirable to block the transcription of the mRNA. In particular, cells may be transformed with sequences complementary to polynucleotides encoding CPEPT. Thus, antisense molecules may be used to modulate CPEPT activity, or to achieve regulation of gene function. Such technology is now well known in the art, and sense or antisense oligomers or larger fragments, can be designed from various locations along the coding or control regions of sequences encoding CPEPT.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding CPEPT. These techniques are described both in Sambrook et al. (supra) and in Ausubel et al. (supra).

Genes encoding CPEPT can be turned off by transforming a cell or tissue with expression vectors which express high levels of a polynucleotide or fragment thereof which encodes CPEPT. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding CPEPT, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding CPEPT.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CPEPT. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of CPEPT, antibodies to CPEPT, mimetics, agonists, antagonists, or inhibitors of CPEPT. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of CPEPT, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example CPEPT or fragments thereof, antibodies of CPEPT, agonists, antagonists or inhibitors of CPEPT, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind CPEPT may be used for the diagnosis of conditions or diseases characterized by expression of CPEPT, or in assays to monitor patients being treated with CPEPT, agonists, antagonists, or inhibitors. The antibodies useful for diagnostic purposes may be prepared in the same manner as those described above for therapeutics. Diagnostics assays for CPEPT include methods which utilize the antibody and a label to detect CPEPT in human body fluids or extracts of cells or tissues. The antibodies may be used with or without modification, and may be labeled by joining them, either covalently or non-covanently, with a reporter molecule. A wide variety of reporter molecules which are known in the art may be used, several of which are described above.

A variety of protocols including ELISA, RIA, FACS for measuring CPEPT are known in the art and provide a basis for diagnosing altered or abnormal levels of CPEPT expression. Normal or standard values for CPEPT expression are established by combining body fluids or cell extracts taken from normal mammalian subjects, preferably human, with antibody to CPEPT under conditions suitable for complex formation. The amount of standard complex formation may be quantified by various methods, but preferably by photometric, means. Quantities of CPEPT expressed in subject samples from biopsied tissues are compared with the standard values. Deviation between standard and subject values establishes the parameters for diagnosing disease.

In another embodiment of the invention, the polynucleotides encoding CPEPT may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of CPEPT may be correlated with disease. The diagnostic assay may be used to distinguish between absence, presence, and excess expression of CPEPT, and to monitor regulation of CPEPT levels during therapeutic intervention.

In one aspect, hybridization with PCR probes which are capable of detecting polynucleotide sequences, including genomic sequences, encoding CPEPT or closely related molecules, may be used to identify nucleic acid sequences which encode CPEPT. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding CPEPT, alleles, or related sequences.

Probes may also be used for the detection of related sequences, and should preferably contain at least 50% of the nucleotides from any of the CPEPT encoding sequences. The hybridization probes of the subject invention may be DNA or RNA and derived from the nucleotide sequence of SEQ ID NO:2 or from genomic sequence including promoter, enhancer elements, and introns of the naturally occurring CPEPT.

Means for producing specific hybridization probes for DNAs encoding CPEPT include the cloning of nucleic acid sequences encoding CPEPT or CPEPT derivatives into vectors for the production of MRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding CPEPT may be used for the diagnosis and treatment of disorders which are associated with expression of CPEPT. Examples of such disorders include diabetes mellitus, galactosialidosis, inflammatory glomerulonephritis, ischemic renal failure, cyclosporine toxicity, endotoxemia, rhabdomyolysis, extracellular matrix accumulation, fibrosis, hypertension, atherosclerosis, coronary vasoconstriction, ischemic heart disease, and lesions occurring in brain disorders such as stroke, trauma, infarcts, progressive multifocal leukoencephalopathy, subacute sclerosing panencephalitis, Alzheimer's disease, Binswanger's disease, Huntington's disease, Parkinson's disease, epilepsy, dementia, multiple sclerosis, neurofibromatosis, and amyotrophic lateral sclerosis. The polynucleotide sequences encoding CPEPT may be used in Southern or northern analysis, dot blot, or other membrane-based technologies; in PCR technologies; or in dip stick, pin, ELISA or chip assays utilizing fluids or tissues from patient biopsies to detect altered CPEPT expression. Such qualitative or quantitative methods are well known in the art.

In a particular aspect, the nucleotide sequences encoding CPEPT may be useful in assays that detect activation or induction of various cancers, particularly those mentioned above. The nucleotide sequences encoding CPEPT may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding CPEPT in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of CPEPT, a normal or standard profile for expression is established. This may be accomplished by combining body fluids or cell extracts taken from normal subjects, either animal or human, with a sequence, or a fragment thereof, which encodes CPEPT, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CPEPT may involve the use of PCR. Such oligomers may be chemically synthesized, generated enzymatically, or produced from a recombinant source. Oligomers will preferably consist of two nucleotide sequences, one with sense orientation (5'–>340) and another with antisense (3'<–5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of CPEPT include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode CPEPT may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding CPEPT on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, CPEPT, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between CPEPT and the agent being tested, may be measured.

Another technique for drug screening which may be used provides for high throughput screening of compounds having suitable binding affinity to the protein of interest as described in published PCT application WO84/03564. In this method, as applied to CPEPT large numbers of different small test compounds are synthesized on a solid substrate, such as plastic pins or some other surface. The test compounds are reacted with CPEPT, or fragments thereof, and washed. Bound CPEPT is then detected by methods well known in the art. Purified CPEPT can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CPEPT specifically compete with a test compound for binding CPEPT. In this manner, the antibodies can be used to detect the presence of any peptide which shares one or more antigenic determinants with CPEPT.

In additional embodiments, the nucleotide sequences which encode CPEPT may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

MPHGNOT03

Peripheral blood was obtained from a 24 year old, Caucasian male. Macrophage cells were separated from heparinized venous blood after centrifugation through Ficoll/Hypaque using HISTOPAQUE-1119 and HISTOPAQUE-10779 (Sigma Diagnostics, St Louis, Mo.). The cells were cultured for 3 to 5 days in Dulbecco's minimum essential medium (DME) supplemented with 10% human serum. After incubation, macrophages mostly adhered to the plastic surface, whereas most other cell types, B and T lymphocytes, remained in solution. The DME was decanted from the wells and washed with phosphate buffered saline (PBS). Macrophages were released from the plastic surface by gently scraping the Petri dishes in PBS/1 mM EDTA and lysed immediately in buffer containing guanidinium isothiocyanate.

The lysate was extracted twice with a mixture of phenol and chloroform, pH 8.0 and centrifuged over a CsCl cushion using a SW28 rotor in a L8-70M Ultracentrifuge (Beckman Instruments). The RNA was precipitated using 0.3 M sodium acetate and 2.5 volumes of ethanol, resuspended in water and DNase treated for 15 min at 37° C. The mRNA was isolated using the OLIGOTEX kit (QIAGEN Inc., Chatsworth, Calif.).

The poly $A^+$ RNA was used to construct the cDNA library. The ECOR I adapted, double-stranded cDNA was digested with Xho I restriction enzyme and fractionated on SEPHACRYL S400 to obtain sequences which exceeded 1000 bp in size. The size-selected cDNAs were inserted into the LAMBDAZAP vector system (Stratagene); and the vector which contains the PBLUESCRIPT phagemid (Stratagene) was transformed into *E. coli,* strain XL1-BLUEMRF (Stratagene).

MMLR3DT01

The peripheral blood macrophages used for this library were obtained from two 24 year old, Caucasian males. This library represents a mixture of allogeneically stimulated human macrophage populations obtained from Ficoll/Hypaque purified buffy coats. The cells from the two different donors (not typed for HLA alleles) were incubated at a density of $1\times10^6$/ml for 72 hours in DME containing 10% human serum.

Cell lysis and RNA preparation were as described previously for MPGHNOT03. The RNA was used in the SUPERSCRIPT plasmid system for cDNA Synthesis and Plasmid Cloning (cat. #18248–013; Gibco BRL, Gaithersburg, Md.) with the recommended protocol. cDNAs were fractionated on a SEPHAROSE CL4B column (Cat. #275105, Pharmacia, Alameda, Calif.), and those cDNAs exceeding 400 bp were ligated into PSPORTI. The plasmid was transformed into chemically competent DH5α host cells (Gibco BRL).

COLNCRTO1

The COLNCRTO1 cDNA library was constructed from a portion of diseased ascending and transverse colon tissue obtained from a 40 year old Caucasian male with Crohn's disease who had undergone a partial colorectomy and anal fistulotomy. Additional diagnoses included functional diarrhea, oral candidiasis, a perianal abscess and a secondary malignant colorectal neoplasm. The patient history indicated type I diabetes mellitus which was being treated with insulin and benign hypertension for which medication was not prescribed. Also reported in the patient history was an episode of unspecified viral meningitis, anorexia, pulmonary insufficiency associated with continuous tobacco use, and repair of an inguinal hernia. At the time of surgery the patient was taking ZANTAC (ranitidine hydrochloride; Glaxo Pharmaceuticals, Research Park Triangle, N.C.) to inhibit gastric acid secretion. Prednisone therapy and ANUSOL (hydrocortisone; Parke-Davis, Morris Plains, N.J.) were also prescribed for treatment of his gastrointestinal disease.

The frozen tissue was homogenized and lysed using a Polytron-PT 3000 homogenizer (Brinkmann Instruments, Inc., Westbury, N.Y.) in guanidinium isothiocyanate solution. The lysate was centrifuged over a 5.7 M CsCl cushion using a SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNase treated at 37° C. The RNA was re-extracted with phenol chloroform pH 8.0 and precipitated using sodium acetate and ethanol as before. The mRNA was then isolated using the OLIGOTEX kit (QIAGEN, Inc. Chatsworth, Calif.) and used to construct the cDNA library.

II Isolation and Sequencing of cDNA Clones

Plasmid DNA was released from the cells and purified using the MINIPREP Kit (Cat. #77468; Advanced Genetic Technologies Corporation, Gaithersburg, Md.). This kit consists of a 96 well block with reagents for 960 purifications. The recommended protocol was employed except for the following changes: 1) the 96 wells were each filled with only 1 ml of sterile Terrific Broth (cat. #22711, GIBCO/BRL, Gaithersburg, Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger, F. and A. R. Coulson (1975; J. Mol. Biol. 94:441f), using a MICROLAB 2200 (Hamilton, Reno, Nev.) in combination with four Peltier thermal cyclers (PTC200 from MJ Research, Watertown, Mass.) and Applied Biosystems 377 or 373 DNA sequencing systems (Perkin Elmer); and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding CPEPT occurs. Abundance and percent abundance are also reported. Abundance directly reflects the number of times a particular transcript is represented in a cDNA library, and percent abundance is abundance divided by the total number of sequences examined in the cDNA library.

V Extension of CPEPT-Encoding Polynucleotides

Nucleic acid sequences of Incyte Clones 443004, 566993, and 774069 were used to design oligonucleotide primers for extending a partial nucleotide sequence to full length. One primer was synthesized to initiate extension in the antisense direction and the other was synthesized to extend sequence in the sense direction (XLF). Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations was avoided. Selected Gibco/BRL cDNA libraries were used to extend the sequence.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M.J. Research, Watertown, Mass.) and the following parameters:

| Step 1  | 94° C. for 1 min (initial denaturation) |
| Step 2  | 65° C. for 1 min |
| Step 3  | 68° C. for 6 min |
| Step 4  | 94° C. for 15 sec |
| Step 5  | 65° C. for 1 min |
| Step 6  | 68° C. for 7 min |
| Step 7  | Repeat step 4–6 for 15 additional cycles |
| Step 8  | 94° C. for 15 sec |
| Step 9  | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 μCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.), hybridization patterns are compared visually.

VII Complementary Polynucleotides

Complementary polynucleotides, fragments, or antisense molecules thereof are used to inhibit in vivo or in vitro expression of naturally occurring CPEPT. Use of complementary oligonucleotides, comprising about 20 base-pairs, is specifically described, essentially the same procedure is used with larger cDNA fragments. An oligonucleotide based on the coding sequences of CPEPT, as shown in FIG. 1, is used to inhibit expression of naturally occurring CPEPT. The complementary oligonucleotide is designed from the most unique 5' sequence as shown in FIG. 1 and used either to inhibit transcription by preventing promoter binding to the upstream nontranslated sequence or translation of an CPEPT-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1.

VIII Expression of CPEPT

Expression of CPEPT is accomplished by subcloning the cDNAs into appropriate vectors and transforming the vectors into host cells. In this case, the cloning vector, PSPORTI, previously used for the generation of the cDNA library is used to express CPEPT in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of CPEPT into the bacterial growth media which can be used directly in the following assay for activity.

IX Demonstration of CPEPT Activity

CPEPT can be expressed by transforming a mammalian cell line such as COS7, HeLa or CHO with an eukaryotic expression vector encoding CPEPT. Eukaryotic expression vectors are commercially available, and the techniques to introduce them into cells are well known to those skilled in the art. A small amount of a second plasmid, which expresses any one of a number of marker genes such as β-galactosidase, is co-transformed into the cells in order to allow rapid identification of those cells which have taken up and expressed the foreign DNA. The cells are incubated for 48–72 hours after transformation under conditions appropriate for the cells to allow expression and accumulation of CPEPT and β-galactosidase.

The serine protease inhibitor [$^3$H] diisopropyl fluorophosphate (DFP) (Du Pont-New England Nuclear) is used to directly detect the presence of CPEPT in transformed cells. The transformed cells are trypsinized, rinsed three times with phosphate-buffered saline, and homogenized in ice-cold water. Cell lysates are adjusted to 0.01 M sodium phosphate, pH 6.8, and freeze-thawed once. 3 µCi of [$^3$H] DFP is added and allowed to bind for 1 hour at room temperature. The lysates are separated by SDS-polyacrylamide gel electrophoresis, visualized by fluorography, and compared to controls.

X Production of CPEPT Specific Antibodies

CPEPT that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring CPEPT Using Specific Antibodies

Naturally occurring or recombinant CPEPT is substantially purified by immunoaffinity chromatography using antibodies specific for CPEPT. An immunoaffinity column is constructed by covalently coupling CPEPT antibody to an activated chromatographic resin, such as CNBR activated SEPHAROSE (Pharmacia & Upjohn). After the coupling, the resin is blocked and washed according to the manufacturer's instructions.

Media containing CPEPT is passed over the immunoaffinity column, and the column is washed under conditions that allow the preferential absorbance of CPEPT (e.g., high ionic strength buffers in the presence of detergent). The column is eluted under conditions that disrupt antibody/CPEPT binding (eg, a buffer of pH 2–3 or a high concentration of a chaotrope, such as urea or thiocyanate ion), and CPEPT is collected.

XII Identification of Molecules Which Interact with CPEPT

CPEPT or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled CPEPT, washed and any wells with labeled CPEPT complex are assayed. Data obtained using different concentrations of CPEPT are used to calculate values for the number, affinity, and association of CPEPT with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide comprising an amino acid sequence selected from the group consisting of:
   a) an amino acid sequence of SEQ ID NO:1, SEQ ID NO:3, or SEQ ID NO:5;
   b) a naturally-occurring amino acid sequence having at least 90% sequence identity to the sequence of SEQ ID NO:1, SEQ ID NO:3, or SEQ ID NO:5, wherein said naturally-occurring amino acid sequence has carboxypeptidase activity; and
   c) a fragment of the amino acid sequence of SEQ ID NO:1, SEQ ID NO:3, or SEQ ID NO:5, wherein said fragment has carboxypeptidase activity.

2. An isolated polypeptide of claim 1, having a sequence of SEQ ID NO:1.

3. An isolated polypeptide of claim 1, having a sequence of SEQ ID NO:3.

4. An isolated polypeptide of claim 1, having a sequence of SEQ ID NO:5.

5. A composition comprising a polypeptide of claim 1 and a pharmaceutically acceptable excipient.

6. A composition of claim 5, wherein the polypeptide has the sequence of SEQ ID NO:1.

7. A composition of claim 5, wherein the polypeptide has the sequence of SEQ ID NO:3.

8. A composition of claim 5, wherein the polypeptide has the sequence of SEQ ID NO:5.

9. An isolated polypeptide of claim 1 which comprises a naturally-ocurring amino acid sequence having at least 90% sequence identity to the sequence of SEQ ID NO:1, wherein said naturally-occurring amino acid sequence has carboxypeptidase activity.

10. A composition comprising a polypeptide of claim 9 and a pharmaceutically acceptable excipient.

11. An isolated polypeptide of claim 1 which comprises a naturally-ocurring amino acid sequence having at least 90% sequence identity to the sequence of SEQ ID NO:3, wherein said naturally-occurring amino acid sequence has carboxypeptidase activity.

12. A composition comprising a polypeptide of claim 11 and a pharmaceutically acceptable excipient.

13. An isolated polypeptide of claim 1 which comprises a naturally-ocurring amino acid sequence having at least 90% sequence identity to the sequence of SEQ ID NO:5, wherein said naturally-occurring amino acid sequence has carboxypeptidase activity.

14. A composition comprising a polypeptide of claim 13 and a pharmaceutically acceptable excipient.

15. A method for producing a polypeptide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1; and
   b) recovering the polypeptide so expressed.

16. A method of claim 15, wherein the polypeptide has the sequence of SEQ ID NO:1.

17. A method of claim 15, wherein the polypeptide has the sequence of SEQ ID NO:3.

18. A method of claim 15, wherein the polypeptide has the sequence of SEQ ID NO:5.

19. A method for screening a compound for effectiveness as an agonist of a polypeptide of claim 1, the method comprising:
   a) exposing a sample comprising a polypeptide of claim 1 to a compound; and
   b) detecting agonist activity in the sample.

20. A method for screening a compound for effectiveness as an antagonist of a polypeptide of claim 1, the method comprising:
   a) exposing a sample comprising a polypeptide of claim 1 to a compound; and
   b) detecting antagonist activity in the sample.

* * * * *